US00PP35572P3

(12) United States Plant Patent
Schoone

(10) Patent No.: US PP35,572 P3
(45) Date of Patent: Jan. 9, 2024

(54) ***PHALAENOPSIS* PLANT NAMED 'WIGGLE GIGGLE'**

(50) Latin Name: *Phalaenopsis hybrida*
Varietal Denomination: Wiggle Giggle

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 18/130,915

(22) Filed: Apr. 5, 2023

(65) Prior Publication Data

US 2023/0329133 P1 Oct. 12, 2023

Related U.S. Application Data

(60) Provisional application No. 63/328,154, filed on Apr. 6, 2022.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
See application file for complete search history.

(56) References Cited

PUBLICATIONS

CPVO Register-CPVO Application Consultation—versions 4.10.7, S2/S3 Publication (Retrieved from the Internet on Jul. 30, 2023). Citation for 'Wiggle Giggle'.*

* cited by examiner

*Primary Examiner* — Susan McCormick Ewoldt
(74) *Attorney, Agent, or Firm* — C. Anne Whealy

(57) ABSTRACT

A new and distinct cultivar of *Phalaenopsis* plant named 'Wiggle Giggle', characterized by its relatively compact and broadly upright plant habit; moderately vigorous growth habit; strong flowering stems; strong leaves; freely flowering habit with typically three inflorescences per plant, each inflorescence with numerous flowers; reddish purple-colored flowers with dark purplish red-colored labellum; and good postproduction longevity.

2 Drawing Sheets

Figure 1:
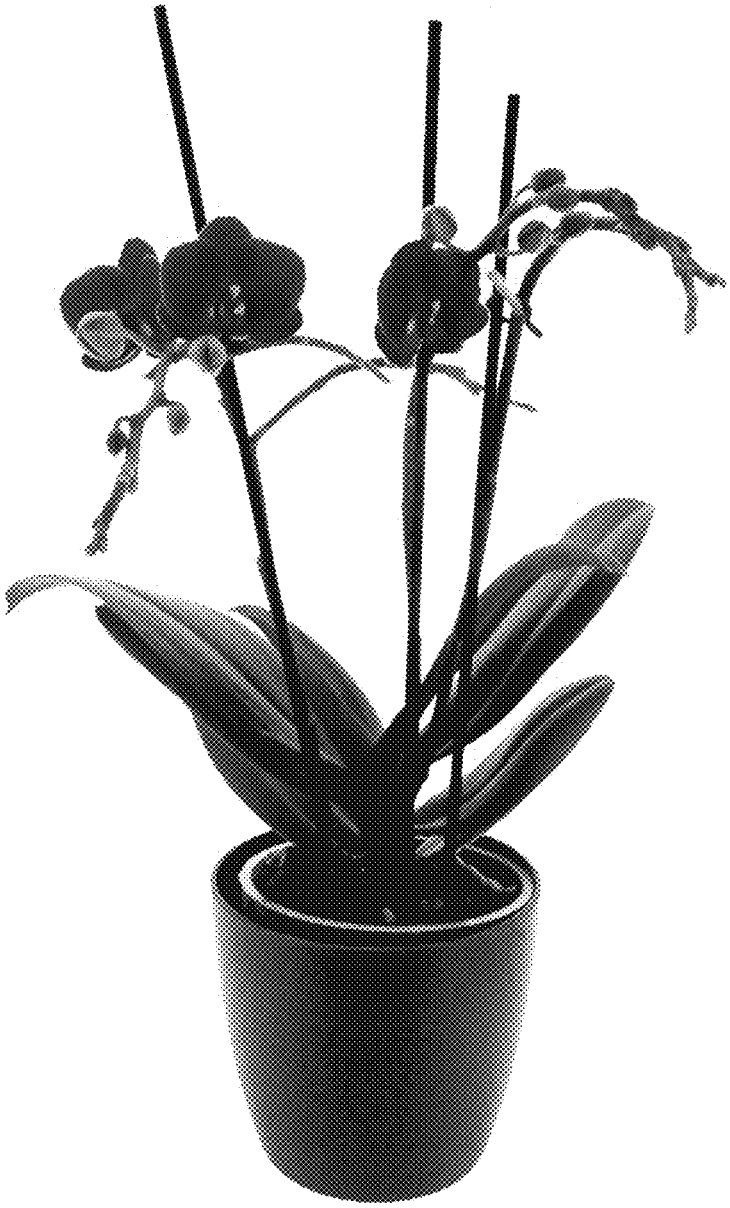

Botanical designation: *Phalaenopsis hybrida.*
Cultivar denomination: 'WIGGLE GIGGLE'.

An European Community Plant Breeder's Rights application for the instant plant was filed by the Applicant/Assignee of the instant application, Floricultura B.V. of Heemskerk, The Netherlands on Mar. 25, 2022, application number 2022/0811. Foreign priority is not claimed to this application.

BACKGROUND OF THE INVENTION

The present invention relates to a new and distinct cultivar of *Phalaenopsis* plant, botanically known as *Phalaenopsis hybrida*, and hereinafter referred to by the name 'Wiggle Giggle'.

The new *Phalaenopsis* plant is a product of a planned breeding program conducted by the Inventor in Nantou, Taiwan and Heemskerk, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in March, 2011 in Nantou, Taiwan of *Phalaenopsis hybrida* 'Sogo Berry', not patented, as the female, or seed, parent with *Phalaenopsis hybrida* 'Little Gem Stripes', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in February, 2019.

Asexual reproduction of the new *Phalaenopsis* plant by in vitro meristem propagation in a controlled environment in Assendelft, The Netherlands since February, 2020 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Wiggle Giggle'. These characteristics in combination distinguish 'Wiggle Giggle' as a new and distinct *Phalaenopsis* plant:

1. Relatively compact and broadly upright plant habit.
2. Moderately vigorous growth habit.
3. Strong flowering stems.
4. Strong leaves.

5. Freely flowering habit with typically three inflorescences per plant, each inflorescence with numerous flowers.
6. Reddish purple-colored flowers with dark purplish red-colored labellum.
7. Good postproduction longevity.

Plants of the new *Phalaenopsis* can be compared to plants of the female parent, 'Sogo Berry'. Plants of the new *Phalaenopsis* differ primarily from plants of 'Sogo Berry' in petal shape as the petal shape of flowers of plants of the new *Phalaenopsis* is more compressed than the petal shape of flowers of plants of 'Sogo Berry'. In addition, flowers of plants of the new *Phalaenopsis* have whiskers (cirrose apices of the labellum) whereas flowers of plants of 'Sogo Berry' do not have whiskers.

Plants of the new *Phalaenopsis* can be compared to plants of the male parent, 'Little Gem Stripes'. Plants of the new *Phalaenopsis* differ primarily from plants of 'Little Gem Stripes' in flower petal color as flower petals of plants of the new *Phalaenopsis* are reddish purple in color with very few stripes whereas flower petals of plants of 'Little Gem Stripes' are white in color with many stripes.

Plants of the new *Phalaenopsis* can be compared to plants of *Phalaenopsis hybrida* 'Kissy Lips', disclosed in U.S. Plant Pat. No. 29,337. In side-by-side comparisons, plants of the new *Phalaenopsis* differ primarily from plants of 'Kissy Lips' in labellum shape as the central lobe of the labellum of flowers of plants of the new *Phalaenopsis* are deltoid to trullate in shape whereas the central lobe of the labellum of flowers of plants 'Kissy Lips' are rounded. In addition, flowers of plants of the new *Phalaenopsis* have whiskers (cirrose apices of the labellum) whereas flowers of plants of 'Kissy Lips' do not have whiskers.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Wiggle Giggle' grown in a container.

Figure 2:
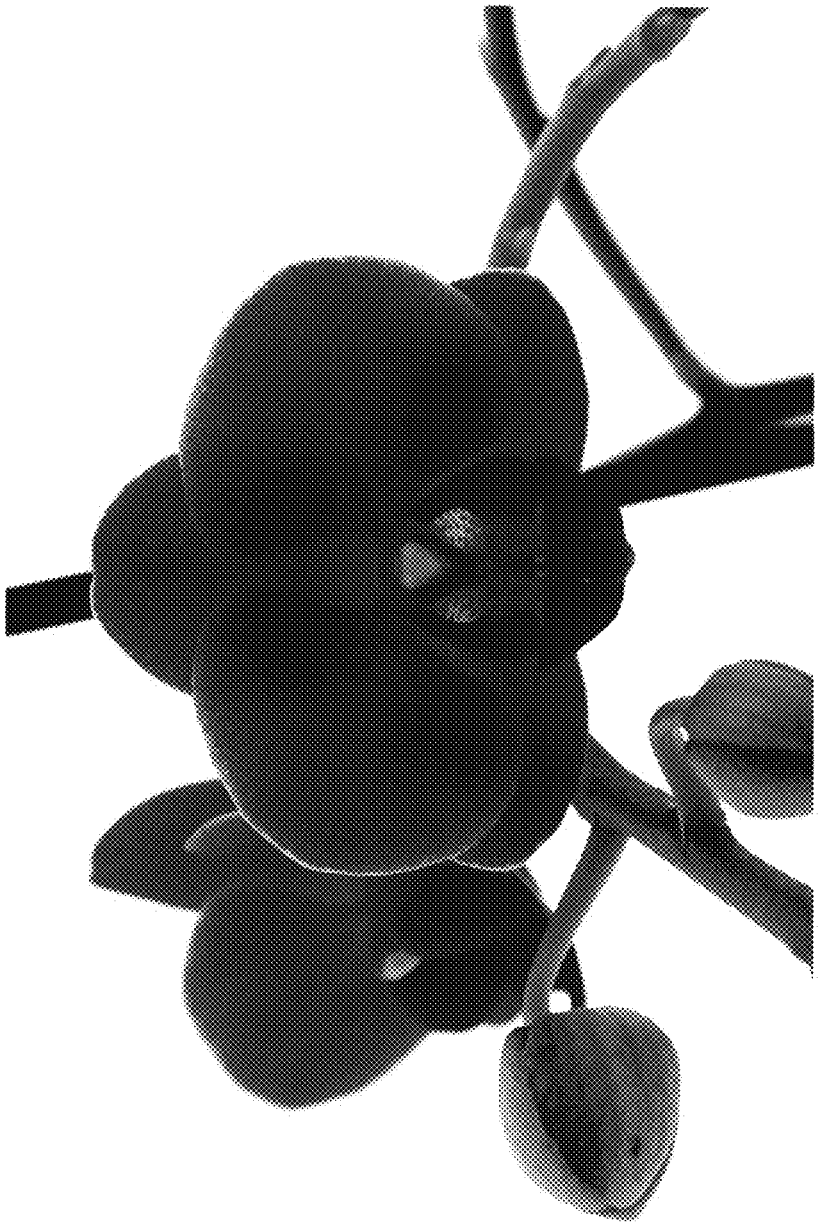

The photograph on the second sheet (FIG. 2) is a close-up view of typical flowers of 'Wiggle Giggle'.

DETAILED BOTANICAL DESCRIPTION

The aforementioned photographs and following observations and measurements describe plants grown during the autumn in 10.5-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27 C. During the final six months of production of the plants, day temperatures ranged from 20 C to 22 C and night temperatures ranged from 18 C to 20 C. During the production of the plants, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Wiggle Giggle'.

Parentage:

*Female, or seed, parent.*—*Phalaenopsis hybrida* 'Sogo Berry', not patented.

*Male parent.*—*Phalaenopsis hybrida* 'Little Gem Stripes', not patented.

Propagation:

*Type.*—By in vitro meristem propagation.

*Time to initiate roots, summer and winter.*—About two weeks at temperatures about 28 C to 30 C.

*Time to produce a rooted young plant, summer and winter.*—About 20 to 25 weeks at temperatures about 28 C to 30 C.

*Root description.*—Thin, fibrous; typically light yellowish white in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; relatively compact and broadly upright plant habit with typically three inflorescences per plant, each inflorescence with numerous flowers; monopodial; moderately vigorous growth habit and moderate growth rate.

*Plant height, substrate level to top of foliar plane.*—About 15.9 cm.

*Plant height, substrate level to top of inflorescences.*—About 27 cm.

*Plant diameter or spread.*—About 26.4 cm.

Leaf description:

*Arrangement and quantity.*—Distichous, simple; sessile; about five leaves per plant.

*Length.*—About 17.6 cm.

*Width.*—About 6.4 cm.

*Aspect.*—Mostly upright to outwardly arching.

*Shape.*—Narrowly obovate to narrowly elliptic-oblong; slightly carinate.

*Apex.*—Unequal acute to short apiculate.

*Base.*—Sheathing. Sheath length: About 1.8 cm. Sheath width: About 1.4 cm. Sheath color: Close to 144A; towards the margins, close to 143A and 143B.

*Margin.*—Entire; not undulate.

*Texture and luster, upper surface.*—Smooth, glabrous; slightly glossy.

*Texture and luster, lower surface.*—Smooth, glabrous; moderately glossy.

*Venation pattern.*—Camptodromous.

*Color.*—Developing leaves, upper surface: Close to a blend of NN137B and 143A. Developing leaves, lower surface: Close to 146B; towards the margins, close to 146A. Fully expanded leaves, upper surface: Close to 137A and NN137B; venation, close to NN137B. Fully expanded leaves, lower surface: Close to 146B; venation, close to a blend of 146A and 146B.

Inflorescence description:

*Appearance and flowering habit.*—Showy zygomorphic flowers arranged on axillary branched racemes; typically three inflorescences per plant; each inflorescence with about 17 flowers; flowers face outwardly on arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about ten weeks on the plant; flowers not persistent.

*Inflorescence length* (*lowermost flower to inflorescence apex*).—About 16 cm.

*Inflorescence width*.—About 10.9 cm.

*Flower buds*.—Height: About 1.8 cm. Diameter: About 1.3 cm by 1.5 cm. Shape: Broadly ovate. Color: Close to N144D and 152D; margins of immature sepals, close to N77B.

*Flower size*.—About 4.4 cm (vertical) by 4.7 cm (horizontal).

*Flower depth*.—About 2.2 cm.

*Petals, quantity and arrangement*.—Three, two lateral petals and one center petal transformed into a labellum.

*Lateral petals*.—Length: About 2.6 cm. Width: About 3 cm. Shape: Roughly reniform to close to lunate. Apex: Obtuse to rounded. Margin: Entire. Texture and luster, upper and lower surfaces: Smooth, glabrous, velvety; matte. Color: When opening, upper surface: Close to a blend of N78A and N79C; narrowly edged, close to N80A; venation, close to N79C. When opening, lower surface: Close to N80A; center, close to N80B; narrowly edged, close to N80A. Fully opened, upper surface: Close to N78A; narrowly edged, close to N80C; venation, close to a blend of N78A and N79C; color does not change with subsequent development. Fully opened, lower surface: Close to N80A; center, close to N80B; narrowly edged, close to N80C; color does not change with subsequent development.

*Labella*.—Appearance: Three-parted with two lateral lobes and a central lobe. Length, lateral lobes: About 1.5 cm. Width, lateral lobes: About 1.1 cm. Length, central lobe: About 2.1 cm. Width, central lobe: About 4 mm to 18 mm. Length, cirrose tips: About 3 mm. Shape, lateral lobes: Obovate. Shape, central lobe: Deltoid to trullate with an elongated apex. Apex, lateral lobes: Obtuse. Apex, central lobe: Cleft with two curved cirrose apices. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 4 mm in length, about 5 mm in width and about 4 mm in height. Color: When opening, upper surface: Lateral lobes: Close to a blend of N78A and N79C; towards the base, close to 71A and at the base, close to 155D. Central lobe: Close to N79C; at the base, close to 155D; radial stripes, close to N79C; cirrose apices, close to N80D to lighter than N80D. Callosities: Close to 12B with fine dots, close to 180B. When opening, lower surface: Close to a blend of N78A and N79C; stripes at the base, close to 71A and 155D. Central lobe: Close to N79C; towards the center and apex, close to N78A; center, blotched with close to 11D and 76B; at the base, close to 156D; cirrose apices, close to N80D to lighter than N80D. Fully opened, upper surface: Lateral lobes: Close to a blend of N78A and N79C; towards the base, close to 71A and at the base, close to 155D. Central lobe: Close to N79C; at the base, close to 155D; radial stripes, close to N79C; cirrose apices, close to N80D to lighter than N80D. Callosities: Close to 13B with fine dots, close to 180B. Fully opened, lower surface: Lateral lobes: Close to a blend of N78A and N79C; stripes at the base, close to 71A and 155D. Central lobe: Close to N79C; towards the center and apex, close to N78A; center, blotched with close to 155D and 76B; at the base, close to 156D; cirrose apices, close to N80D to lighter than N80D.

*Sepals*.—Quantity and arrangement: Three, one upper dorsal sepal and two lower lateral sepals. Length, dorsal and lateral sepals: About 2.7 cm. Width, dorsal sepal: About 2.2 cm. Width, lateral sepal: About 2.1 cm. Shape, dorsal and lateral sepals: Broadly ovate. Apex, dorsal sepal: Shallowly and broadly retuse. Apex, lateral sepals: Obtuse. Base, dorsal and lateral sepals: Truncate. Margin, dorsal and lateral sepals: Entire. Texture and luster, dorsal and lateral sepals, upper and lateral surfaces: Smooth, glabrous, moderately velvety; matte. Color, dorsal sepal: When opening, upper surface: Close to a blend of N78A and N79C; towards the margins, close to N78A and narrowly edged, close to N80D; venation, close to N79C. When opening, lower surface: Close to 145C; fine dots, close to 77B; towards the margins, close to 77B and narrowly edged, close to N80D. Fully opened, upper surface: Close to N78A; towards the margins, close to N78B and narrowly edged, close to N80D; venation, close to N79C; color does not change with subsequent development. Fully opened, lower surface: Close to 196B; towards the margins, close to 77B and narrowly edged, close to N80D; color does not change with subsequent development. Color, lateral sepals: When opening, upper surface: Upper half, close to N78A and lower half, close to N79C; blotch at the base of the lower half, close to 157B; fine dots, close to N79C; narrowly edged with close to N80D; venation, close to N79C. When opening, lower surface: Close to 145B; towards the margins, lighter than close to a blend of 77B and 77D and narrowly edged, close to N80D. Fully opened, upper surface: Upper half, close to a blend of N78A and N79C and lower half, close to N79C; blotch at the base of the lower half, close to 157B; fine dots, close to N79C; narrowly edged with close to N80D; venation, close to N79C; color does not change with subsequent development. Fully opened, lower surface: Close to 145B to 145C; towards the margins, lighter than close to 77B and narrowly edged, close to N80D; color does not change with subsequent development.

*Peduncles*.—Length: About 39.7 cm. Diameter: About 5 mm. Strength: Strong. Aspect: Upright to outwardly arching. Texture and luster: Smooth, glabrous; matte. Color: Close to 138A; densely covered with fine dots and marbling, close to 137A.

*Pedicels*.—Length: About 2.3 cm. Diameter: About 3 mm. Strength: Moderately strong. Aspect: About 90 degrees from peduncle axis. Texture and luster: Smooth, glabrous; matte. Color: Close to 144B; distally, close to 145B.

*Reproductive organs*.—Androecium: Column length: About 8 mm. Column width: About 5 mm. Column color: Close to N78A; distally, tinged with close to NN78A. Pollinia quantity: Two. Pollinia diameter (per two pollinia): About 2 mm. Pollinia color: Close to 23A. Gynoecium: Stigma length: About 3 mm. Stigma width: About 4 mm. Stigma shape: Reniform. Stigma color: Close to 76C to 76D. Ovary length: About 7 mm. Ovary diameter: About 1 mm. Ovary color: Close to N144B. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40 C and are suitable for USDA Hardiness Zones 10 to 12.

It is claimed:

1. A new and distinct *Phalaenopsis* plant named 'Wiggle Giggle' as illustrated and described.

* * * * *